US00PP26818P3

(12) United States Plant Patent
Bédard

(10) Patent No.: US PP26,818 P3
(45) Date of Patent: Jun. 14, 2016

(54) GRANDIFLORA ROSE PLANT NAMED 'WEKSTOHOCO'

(50) Latin Name: *Rosa hybrida*
Varietal Denomination: WEKstohoco

(71) Applicant: Early Morning LLC, Pomona, CA (US)

(72) Inventor: Christian Bédard, Placentia, CA (US)

(73) Assignee: EARLY MORNING LLC, Pomona, CA (US)

( * ) Notice: Subject to any disclaimer, the term of this patent is extended or adjusted under 35 U.S.C. 154(b) by 118 days.

(21) Appl. No.: 13/998,586

(22) Filed: Nov. 14, 2013

(65) Prior Publication Data

US 2015/0135375 P1 May 14, 2015

(51) Int. Cl.
*A01H 5/02* (2006.01)

(52) U.S. Cl.
USPC ..... Plt./130

(58) Field of Classification Search
USPC ..... Plt./130
See application file for complete search history.

(56) References Cited

U.S. PATENT DOCUMENTS

PP11,384 P 5/2000 Carruth
PP11,691 P 12/2000 Zary
PP15,155 P2 9/2004 Carruth

*Primary Examiner* — Keith Robinson
(74) *Attorney, Agent, or Firm* — McKee, Voorhees & Sease, PLC

(57) ABSTRACT

A new variety of Grandiflora rose suitable for garden decoration, having flowers of creamy white coloration blushing coral-orange.

1 Drawing Sheet

Classification: The present invention relates to a new *Rosa hybrida* plant.

Variety denomination: The new plant has the varietal denomination 'WEKstohoco'.

BACKGROUND OF THE INVENTION

This invention relates to a new and distinct variety of Grandiflora Rose. It has as its seed parent the variety known as 'WEKcryland' (U.S. Plant Pat. No. 11,384) and as its pollen parent the variety known as 'WEKpaltlez' (U.S. Plant Pat. No. 15,155).

SUMMARY OF THE INVENTION

Among the features which distinguish the new variety from other presently available and commercial rose cultivars known to the inventor are the following combinations of characteristics: its unusual creamy white blushing coral-orange flower coloration, its many hairs on the peduncle, its rough rachis with some stipitate glands and small prickles and its red suffusion on the inner surface of the sepal that appears as the flower ages. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKstohoco' may be asexually propagated by cuttings, budding and grafting. The budding and grafting successfully occurred on the plant/rootstock *Rosa hybrida* cv. 'Dr. Huey' (not patented). The exterior root color is between 177B and 200D. Roots formation will start within 7 days and the cuttings will be rooted within 21 days.

COMPARISON WITH PARENTS

The new rose may be distinguished from its seed parent, 'WEKcryland' by the following combination of characteristics: whereas 'WEKstohoco' bears double flowers (about 20 to 31 petals) of creamy white coloration blushing coral-orange, 'WEKcryland' bears double flowers of white coloration with a very fine pink edging with significantly heavier petalage (about 34 to 42 petals). The new variety bears medium size flowers (about 7.3 to about 9.5 cm. in diameter), whereas the seed parent bears significantly larger flowers (about 10 to about 12.5 cm. in diameter).

The new variety may be distinguished from its pollen parent, 'WEKpaltlez' by the following combination of characteristics: whereas 'WEKstohoco' bears double flowers (about 20 to 31 petals) of creamy white coloration blushing coral-orange, 'WEKpaltlez' bears double flowers of smoky chocolate orange coloration overlaid with a wash of lavender with lesser petalage (about 17 to 27 petals). The new variety is classified as a Grandiflora rose with an upright moderately spreading medium height growing habit (about 135 to about 175 cm. in height), whereas the pollen parent is classified as a Floribunda rose with a bushy upright significantly taller growing habit (about 170 to about 210 cm. in height).

COMPARISON WITH THE CLOSEST COMMERCIALLY AVAILABLE CULTIVAR

The new variety may be distinguished from its closest commercially available cultivar, 'JACnepal' (U.S. Plant Pat. No. 11,691) by the following combination of characteristics: whereas 'WEKstohoco' bears double flowers (about 20 to 31 petals) of creamy white coloration blushing coral-orange, 'JACnepal' bears double flowers of cream coloration blushing coral pink with heavier petalage (about 30 to 35 petals). The new variety bears medium size flowers (about 7.3 to about 9.5 cm. in diameter), whereas the closest commercially available cultivar bears significantly larger flowers (about 13 to about 14 cm. in diameter).

BRIEF DESCRIPTION OF ILLUSTRATION

The accompanying photograph illustrates the new variety and shows the flowering thereof from bud to full bloom depicted in color as nearly correct as it is possible to make in a color illustration of the character.

The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong short to medium length stems (about 15 to about 45 cm.). Outdoors, the plant blooms abundantly and nearly continuously during the growing season. The flowers have a moderate tea to spicy fragrance.

BUD

The peduncle is about 2.3 to about 5.4 cm. in length, of average caliper (about 0.2 to about 0.3 cm. in diameter), and usually erect. It is smooth with many hairs. Peduncle color is between 146B and 144A sometimes lightly suffused, especially on the side exposed to the sun, with between 187A and 187B.

Before the calyx breaks, the bud is about 1.2 to about 1.5 cm. in diameter at the widest point, about 1.2 to about 2.1 cm. in length, and pointed to somewhat ovoid in shape. The surface of the bud bears between 9 to 12 foliaceous appendages and some hairs, usually with slender entire foliaceous parts extending beyond the tip of the bud about ¾ or more of its length. Bud color is between 137B and 137C often heavily suffused, especially on the side exposed to the sun, with between 187A and 187B.

The sepals are about 2.9 to about 4.0 cm. in length and about 0.7 to about 1.2 cm. in width at the widest point. The outer surface color of the sepal is between 137B and 137C often heavily suffused, especially on the side exposed to the sun, with between 187A and 187B. The outer surface of the sepal is smooth and bears between 0 to 5 foliaceous appendages with some hairs. The inner surface color of the sepal is near 146C broadly bordered by near 137A. After the sepals open, the inner surface color is often heavily suffused, especially on the area exposed to the sun, with between 187A and 187B. The inner surface of the sepal is covered with fine wooly tomentum; sepal margins are lined with few stipitate glands and many hairs.

The receptacle of the flower is of moderately long length (about 0.7 to about 0.9 cm.) and somewhat thin in caliper (about 0.7 to about 0.9 cm. in diameter). The receptacle is cup-shaped in form. Its surface is smooth with few hairs and with somewhat thin fleshy walls. The receptacle color is between 146B and 137B.

As the petals open (after the calyx breaks), the bud is about 1.6 to about 2.2 cm. in diameter at the widest point, about 2.3 to about 3.5 cm. in length, and ovoid to somewhat pointed in form. The color of the under surfaces of the newly opened petals is between 1C and 2D sometimes moderately streaked with between 187B and 53B to as dark as 187A in the middle of the petal and blushed with between 60A and 60B toward the petal edge. There is no visible change in coloration at the point where the petal attaches. The color of the upper surfaces of the newly opened petals is between 1D and 8D blushed with between 53C and 53D toward the petal edge. There is no visible change in coloration at the point where the petal attaches.

BLOOM

When fully open, the bloom ranges from about 7.3 to about 9.5 cm. in diameter. Petalage is double with about 20 to 31 petals and about 1 to 9 petaloids irregularly arranged. When partially open, the bloom form is high centered to somewhat cupped, and the petals are loosely spiraled to somewhat cupped with petal edges somewhat reflexed outward. When fully open, the bloom form is cupped, and the petals are loosely cupped with petal edges somewhat reflexed outward. The undulation of the petal is absent.

PETALS

The substance of the petals is moderately heavy and of medium to somewhat thick thickness, with upper surfaces moderately satiny and under surfaces matte to slightly shiny. The petals are about 2.6 to about 5.1 cm. in length and about 1.8 to about 5.3 cm. in width at the widest point. Petal margins are entire.

The outer petals are nearly round to somewhat obovate in shape with rounded to sometimes slightly mucronate apices.

The inner petals are moderately obovate to somewhat oblanceolate in shape with rounded to sometimes slightly mucronate apices. Thus, incisions of the petal is absent.

Petaloids are about 0.7 to about 3.2 cm. in length and about 0.4 to about 2.8 cm. in width at the widest point. Petaloids are irregularly shaped moderately obovate to somewhat oblanceolate with rounded apices.

NEWLY OPENED FLOWER

The under surface color of the outer petals is between 4D and 158C sometimes moderately suffused with between 46C and 45B to as dark as near 46A and blushed with between 60B and 43B toward the petal edge. There is no visible change in coloration at the point where the petal attaches. The upper surface color of the outer petals is between 4D and 158C blushed with between 60C and 43B to as dark as between 53B and 45A toward the petal edge. There is no visible change in coloration at the point where the petal attaches.

The under surface color of the intermediate and inner petals is between 4D and 158C blushed with between 60B and 43B toward the petal edge. The upper surface color of the intermediate and inner petals is between 4D and 158C blushed with between 60C and 43B toward the petal edge.

The under and upper surface colors of the petaloids are similar in coloration to the upper and under surfaces of the intermediate and inner petals.

The general tonality of the newly opened flower is between 4D and 158C blushed with between 60B and 43B toward the petal edge.

THREE-DAY-OLD FLOWER

The under surface color of the outer petals is between 155A and 155B often heavily suffused with between 53C and 53B to as dark as between 187A and 187B and blushed with between 61A and 45B toward the petal edge. There is no visible change in coloration at the point where the petal attaches. The upper surface color of the outer petals is between 155A and 155B blushed with between 53C and 45B to as dark as between 187B and 187A toward the petal edge. There is no visible change in coloration at the point where the petal attaches.

The under surface color of the intermediate and inner petals is between 4D and 158C sometimes moderately suffused with between 53C and 53B and blushed with between 61A and 45B toward the petal edge. The upper surface color of the intermediate and inner petals is between 4D and 158C blushed with between 60D and 42C to as dark as between 53C and 45B toward the petal edge.

The under and upper surface colors of the petaloids are similar in coloration to the upper and under surfaces of the intermediate and inner petals.

The general tonality of the three-day-old flower is between 4D and 158C blushed with between 60D and 42C to as dark as between 53C and 45B toward the petal edge.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 160) and are arranged regularly about the pistils; a few are mixed with petaloids. The filaments are of somewhat short to medium length (about 0.5 to about 1.0 cm.) most with anthers. Filaments are between 2D and 4D in color. The anthers are of medium size for the class and all open approximately at the same time. Anther color when immature is near 22B on the external part and near 11C on the internal part. Anther color at maturity is near 165C on the external part and near 200B on the internal part. Pollen is moderate and between 18C and 19C in color.

FEMALE REPRODUCTIVE ORGANS

Pistils vary in number (average about 115). The styles are moderately uneven, somewhat long in length (about 0.5 to about 0.9 cm.), average in caliper, and loosely bunched. Stigma color is between 11B and 10B. Style color is between 154C and 150C often heavily suffused, mostly on the upper half, with between 53A and 53B. Ovaries are usually all enclosed in the calyx. The ovaries are of medium size and between 158D and 159D in color.

Hips are of moderately short length (about 1.0 to about 1.4 cm.), moderately globular in form, and between 30B and 30C in color when ripe. The hip surface is smooth with thick fleshy walls. The sepals are fugacious, and usually straight in shape.

The seeds are irregularly rounded, smooth in texture, approximately 3 to about 8 per hip, about 0.3 to about 0.6 cm. in diameter at the widest point and between 164B and 165C in color.

FOLIAGE

The compound leaves are usually comprised of three to seven leaflets and are borne abundantly. The seven-leaflet leaves are about 12.9 to about 17.9 cm. in length and about 10.9 to about 13.6 cm. in width at the widest point, moderately crisp to somewhat leathery in texture on both the upper side and underside, and glossy in finish on the upper side and matte to somewhat semi-glossy in finish on the underside. The leaves have a pinnate venation pattern. The terminal leaflets are about 5.5 to about 8.6 cm. in length and about 3.4 to about 4.9 cm. in width at the widest point, shaped ovate to somewhat oval with acute to somewhat acuminate apices and rounded bases. Their margins are usually simply serrate.

The upper surface color of the mature leaf is between 139A and 146A. The under surface color of the mature leaf is between 147B and 137B. The under and upper colors of the leaf veins on the mature leaf are similar in coloration to the upper and under surfaces colors of the mature leaf. The upper surface color of the young leaf is between 137C and 146A, often moderately suffused with between 187A and 187B. The under surface color of the young leaf is between 137D and 146A, often heavily suffused with between 187B and 187A. The under and upper colors of the leaf veins on the young leaf are similar in coloration to the upper and under surfaces colors of the young leaf.

The rachis is somewhat heavy in caliper and rough. The upper side is shallowly grooved with few hairs and stipitate glands on the edges of the grooves. The under side of the rachis is rough with some stipitate glands and small prickles. The rachis color is near 146D on the underside and near 137B on the upper side often moderately suffused on the young leaves with between 187B and 183A.

The stipules are about 1.4 to about 2.1 cm. in length and moderately wide (about 0.5 to about 0.7 cm.) with long straight points that usually turn out at an angle of more than 45 degrees and sometimes recurve toward the stem. The under and upper surface color of the stipule is between 137C and 138A often moderately suffused on the young leaves with between 187B and 183A. The upper and under surfaces of the stipules are smooth.

The petiole is somewhat heavy in caliper and rough. The upper side is shallowly grooved with few hairs and stipitate glands on the edges of the grooves. The under side of the petiole is rough with some stipitate glands and small prickles. The petiole is about 0.6 to about 1.5 cm. in length and about 0.1 to about 0.2 cm in width at the widest point. The petiole color is near 146D on the underside and near 137B on the upper side often moderately suffused on the young leaves with between 187B and 183A. The petiole and the peduncle are strong and rigid.

The plant displays an above average degree of resistance to powdery mildew (*Sphaerotheca pannosa*) and rust (*Phragmidium* spp.) as compared to other commercial varieties grown under comparable conditions in Pomona, Calif. The plant's winter hardiness and drought/heat tolerance are yet to be determined.

GROWTH

The plant has an upright moderately spreading medium height growing habit (about 135 to about 175 cm. in height and about 160 to about 200 cm. spread at the widest point), with full branching. It displays moderately vigorous growth and the canes are of somewhat heavy caliper for the class (about 1.7 to about 3.3 cm. in diameter at the widest point).

The color of the major stems is between 146A and 146B. They bear many large prickles that are about 0.6 to about 0.9 cm. in length. The large prickles are angled moderately downward with a long narrow oval base; prickle color is between 177C and 166C. The major stem bears some small prickles of similar shape and coloration.

The color of the branches is between 137C and 146A sometimes lightly suffused with between 187B and 187A. They bear some large prickles which are of similar size and shape to the large prickles on the major stems; prickle color is between 152C and 153B often moderately suffused with between 187B and 187C. The branches bear some small prickles of similar shape and coloration.

The color of the new shoots is between 146B and 146A often heavily suffused with between 187B and 187A. They bear some large prickles which are of similar shape to the large prickles on the major stems. The prickles are about 0.4 to about 0.5 cm. in length. The prickle color is between 152C and 153B often heavily suffused with between 187A and 187B. The shoots bear some small prickles of similar shape and coloration. The major stems, branches and new shoots are rough and bear large and small prickles.

I claim:

1. A new and distinct Grandiflora rose plant of the variety substantially as described and illustrated herein.

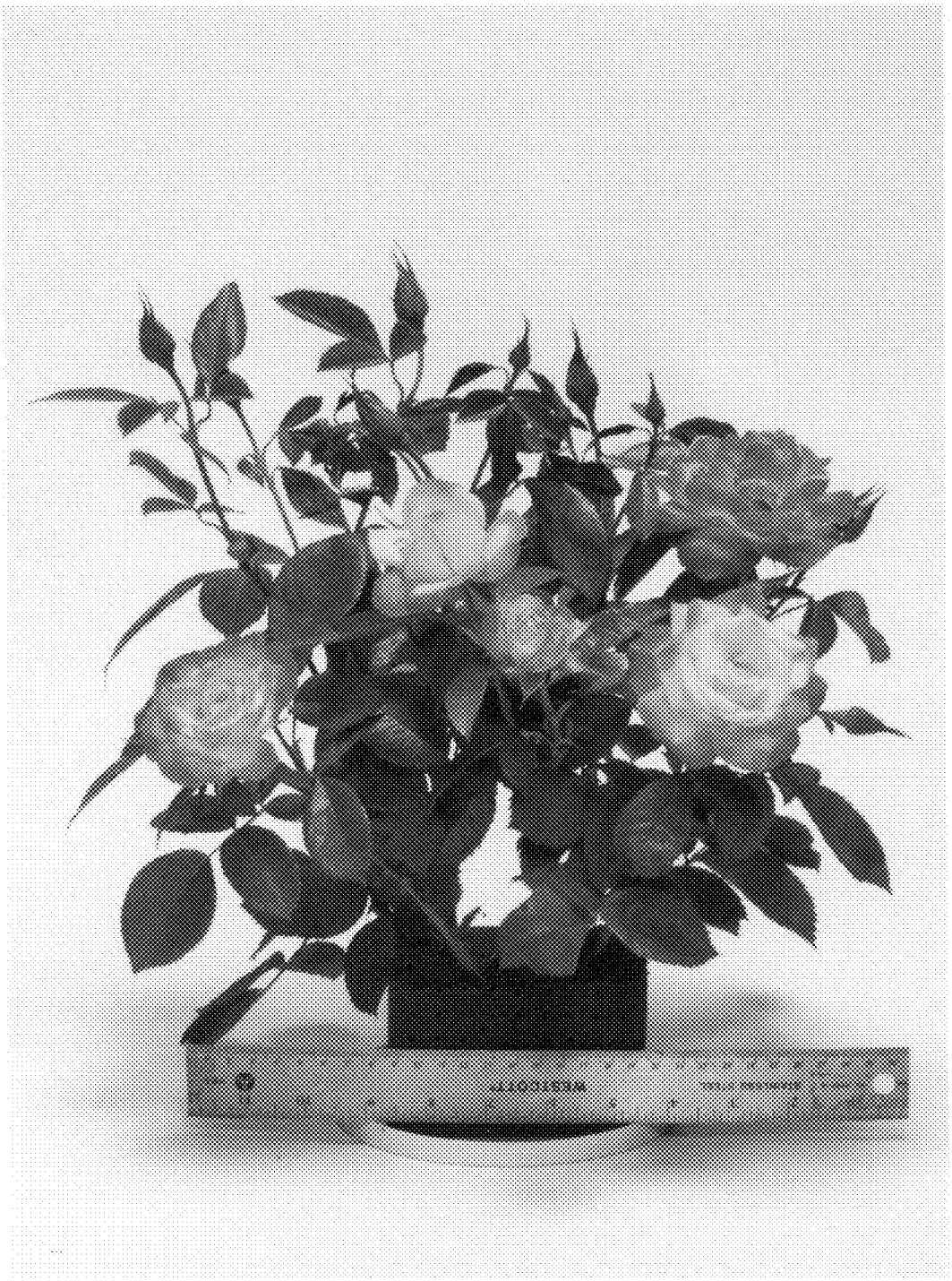

* * * * *